United States Patent [19]

Kaufman

[11] 4,436,098

[45] Mar. 13, 1984

[54] NEEDLE ASSEMBLY WITH VEIN ENTRY INDICATOR

[75] Inventor: Joseph Kaufman, Emerson, N.J.

[73] Assignee: Becton Dickinson Company, Paramus, N.J.

[21] Appl. No.: 244,408

[22] Filed: Mar. 16, 1981

[51] Int. Cl.³ .............................................. A61B 5/14
[52] U.S. Cl. .................................... 128/766; 128/770; 128/771; 604/199; 604/238
[58] Field of Search ............... 128/770, 771, 763–767, 128/218 NV, 220; 137/67; 604/192, 199, 238

[56] References Cited

U.S. PATENT DOCUMENTS

| | | | |
|---|---|---|---|
| 2,735,430 | 2/1956 | Huber | 128/218 NV |
| 2,798,487 | 7/1957 | Ferguson | 128/771 |
| 3,187,749 | 6/1965 | Sarnoff | 128/218 NV |
| 3,240,209 | 3/1966 | Ogle | 128/218 NV |
| 3,585,984 | 6/1971 | Buchanan | 128/276 |
| 3,817,240 | 6/1974 | Ayres | 128/771 |
| 4,166,450 | 9/1979 | Abramson | 128/764 |
| 4,207,870 | 6/1980 | Eldridge | 128/766 |
| 4,295,477 | 10/1981 | Christinger | 128/766 |
| 4,312,362 | 1/1982 | Kaufman | 128/771 |

FOREIGN PATENT DOCUMENTS 2070358 9/1971 France .................. 128/218 NV

Primary Examiner—Edward M. Coven
Assistant Examiner—Max F. Hindenburg
Attorney, Agent, or Firm—Robert P. Grindle

[57] ABSTRACT

A needle assembly preferably suitable for single sample blood collection and for determining vein entry when collecting a blood sample from a patient into a vacuum collection device. This assembly includes a housing with an interior chamber having a blood inlet needle on one side of the housing and a blood outlet needle on the other. The outlet needle extends interiorly into the chamber, is open at its distal end and includes a side hole therethrough. A vent plug covers the side hole by surrounding the outlet needle inside the chamber, while a sealant plug covers the open end of the outlet needle. This arrangement prevents liquid from flowing into the holes while allowing gas to flow through the vent plug into the side hole for escape from the assembly whereby the prevented liquid may then be viewed by a user through a transparent portion of the housing. The sealant plug is removable under the influence of a negative pressure gradient applied through the outlet needle so that this sealant plug is withdrawn into the outlet needle and then liquid is allowed to flow into the outlet needle for collection.

6 Claims, 5 Drawing Figures

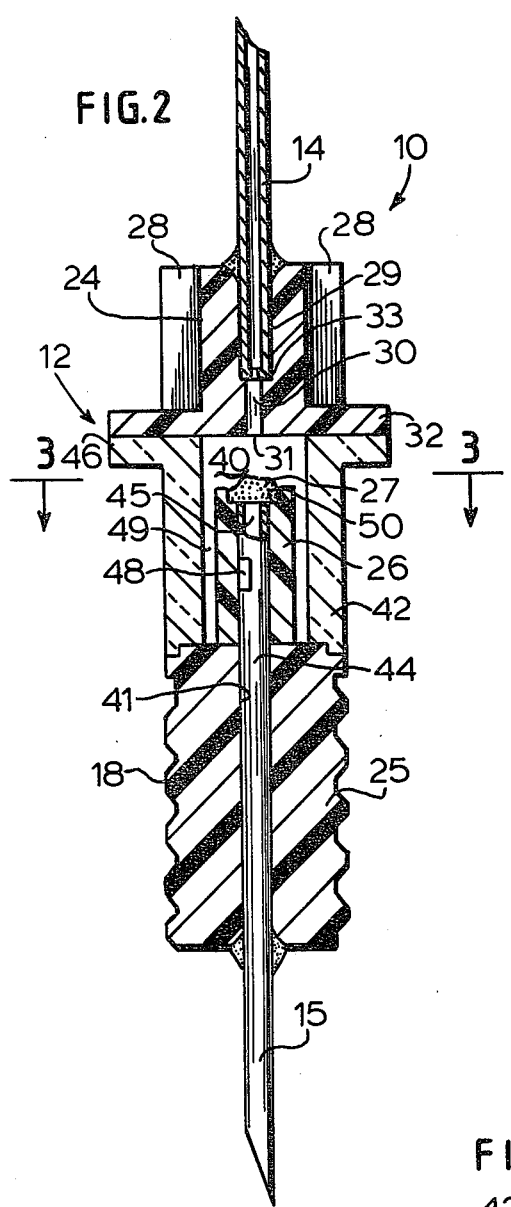
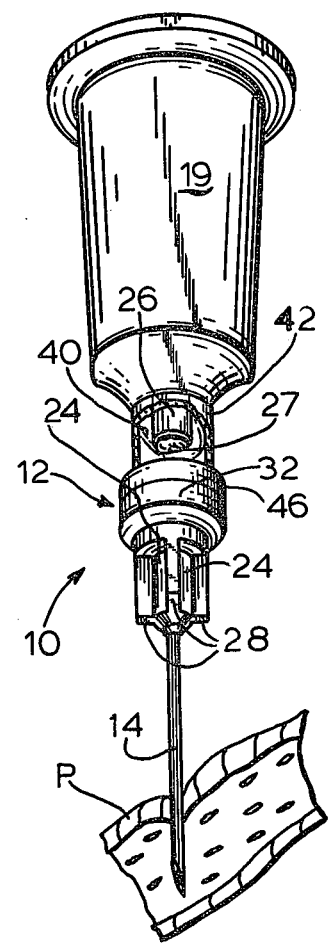
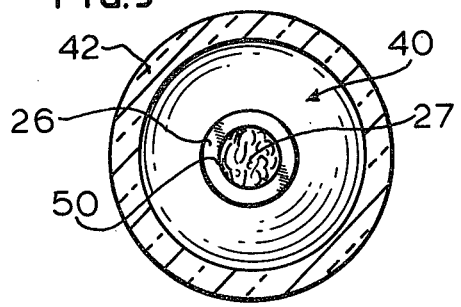

NEEDLE ASSEMBLY WITH VEIN ENTRY INDICATOR

BACKGROUND OF THE INVENTION

1. Field of the Invention

The present invention relates to a needle assembly for collecting fluid, and more particularly, concerns a needle assembly for collecting a single sample of blood from a patient while providing an indication of entry of the needle assembly into the vein of the patient.

2. Description of the Prior Art

In the collection of body fluids, such as blood from a patient, the nurse or clinician collecting this fluid oftentimes must probe for or guess the location of the patient's vein. For instance, the nurse attempting to collect a blood sample, even with tourniquet pressure applied, cannot readily insert the needle in patients who have small veins or if the veins are not close to the skin surface. In those instances, the needle may either miss the vein entirely or perhaps may pass completely through a thin vein. As a result, blood flow through the needle into the evacuated blood collection tube would be uncomfortable and inefficiently slow since the blood would not be flowing from the patient's vein. The nurse would have to start over again and perhaps use another evacuated blood collection tube on the next attempt which, of course, would be wasteful of both materials and expense, not to mention the discomfiture which the patient experiences.

In order to reduce the waste of evacuated blood collection tubes which occurs in the blood collecting procedure where the nurse must guess at vein location, a number of blood collecting devices have been proposed which provide an indicator to the user that satisfactory vein entry has been accomplished. In these visual indicator devices, an antechamber is generally provided which is kept isolated by some sort of valving mechanism from the opening of the needle which deposits the blood being collected into the evacuated tube. Once the nurse probes for the vein and satisfactory entry is made, blood is supposed to flow through the needle into the antechamber to provide a telltale trace that the vein has been properly located. At this point in the blood collecting procedure, an evacuated blood collection tube is then usually inserted into the blood collection holder, opening up some type of valve whereby blood is then free to flow into the evacuated blood collection tube. Typical of these visual indicator blood collection devices are those found in U.S. Pat. Nos. 4,166,450 and 3,585,984.

Although in theory, this antechamber approach for the telltale trace of blood flow is workable, and oftentimes may work satisfactorily, there are, nevertheless, some inherent problems with this approach. For example, the antechamber generally is filled with air at the time the forward end of the needle is inserted into the vein of the patient. Inasmuch as the opposite end of the needle, for puncturing the evacuated blood collection tube, is valved or closed, the air in the antechamber forms a blockage since there is no place for such air to be displaced. Thus, even if the nurse locates the vein, and satisfactory entry is made with normal tourniquet pressure, the blood flow from the patient may not travel all the way through the needle before reaching the antechamber. This is due to the fact that the air in the antechamber blocks the blood flow through the needle even under normal tourniquet pressure. The net result of this is that the nurse will be deceived into believing that satisfactory vein entry has not been accomplished since no telltale trace will be visually observed. Unnecessary secondary venipuncture may take place which, again, is not only uncomfortable to the patient but is inefficient and wasteful.

Accordingly, improved approaches for providing a visual indicator to the user of a blood collecting device are still being sought. These improvements are needed in those types of blood collecting devices which make entry into the vein of the patient before the evacuated blood collection tube is inserted into the blood collection holder, which now is a very common blood collecting procedure.

SUMMARY OF THE INVENTION

A needle assembly for determining fluid access when collecting a fluid sample from a source of fluid into a vacuum collection device comprises a housing with a chamber therein and having first and second access means therethrough in fluid communication with the chamber. The housing includes means for viewing the contents inside the chamber, with the second access means adapted for fluid communication with a vacuum collection device. Means extends into the chamber for directing passage of gas and liquid into the second access means. Means operatively plugs the extension means to prevent liquid from flowing into the extension means while allowing gas to flow into the extension means before the vacuum is applied. The prevented liquid may be viewed by a user through the viewing means. Included with the plug means is sealant means removable from the extension means under the influence of a negative pressure gradient, such as from the vacuum source. This allows liquid to flow into the extension means whereby it may be collected from the second access means.

In a preferred embodiment of the needle assembly of the present invention as generally set forth above, the housing is translucent and has a forward end, a rearward end and a chamber within. A first cannula extends outwardly from the forward end of the housing in fluid communication with the chamber. A second cannula has an exterior portion extending outwardly from the rearward end of the housing and also has an interior portion extending inwardly into the chamber with an open distal end and a side hole therethrough. A vent plug of air-permeable, blood-impermeable, porous material is in liquid-tight contact with the outer surface of the interior portion of the second cannula. This vent plug overlies the side hole and preferably forms a pocket around the open end of the interior portion of the second cannula. A removable mass of compliant plug material is positioned in the pocket and covers the open distal end of the interior portion. Under normal tourniquet pressure, blood flows into the chamber from the first cannula and is prevented by the plugs from flowing into the second cannula but can be viewed by a user through the translucent housing to indicate vein entry by the first cannula. Any air initially in the chamber passes through the vent plug and into the side hole for removal from the assembly. The sealant plug is adapted to be drawn through the distal open end into the second cannula under the influence of a negative pressure gradient applied to the second access opening to thereby uncover the open end of this second cannula. As a result, blood may flow through the open distal end and into the second cannula for collection into the blood collection container.

In accordance with the principles of the present invention, there are structural elements and features herein which are notably different from prior inventions of this type. For instance, the vent and sealant plugs inside the chamber and against the interior cannula serve as a valve mechanism to prevent blood from flowing out of the chamber when the patient needle has been inserted into the vein of the patient. At this point of the blood collecting procedure, the evacuated blood collection tube is normally not yet in position. Therefore, at this point blood should not be allowed to escape from the needle assembly. However, once the nurse makes entry into the patient's vein blood will flow through the forward needle and enter the chamber inside the needle assembly. The nature of the plug materials will prevent any blood flow through the chamber. However, inasmuch as the vent plug material is air-permeable, air either initially in the chamber or in the forward needle will be allowed to escape from the chamber and needle assembly to eliminate the blockage which occurs in prior art needle assemblies proposed for visual indicator operation. Moreover, the sealant plug material is removable from the interior cannula inside the chamber so that when the evacuated blood collection tube is attached to the other side of the needle assembly, the negative pressure gradient will cause the sealant plug to be drawn inside the interior cannula thereby exposing the open distal end in the collection cannula to the blood flow path. In this fashion, as soon as the evacuated blood collection tube is attached, the sealant plug removal effects a valve opening thereby allowing the blood to flow through the needle assembly and into the blood collection container.

Advantageously, the present invention eliminates the deficiencies of the air blockage problem as set forth above with respect to prior art needle assemblies. In this regard, the present invention allows the user to visually observe the trace of blood entering into the chamber inside the needle assembly as soon as the vein has been properly entered, since any air inside the needle assembly is allowed to escape, thereby permitting the free flow of blood into the chamber.

BRIEF DESCRIPTION OF THE DRAWINGS

FIG. 2 is an enlarged cross-sectional view taken along line 2—2 of FIG. 1;

FIG. 3 is an end view of the preferred vent plug and sealant plug for use in the chamber of the embodiment of FIG. 1 taken along line 3—3 of FIG. 2;

FIG. 4 is a perspective view of the needle assembly connected to a holder and inserted into a patient so that a user can view same for indication of vein entry.

DESCRIPTION OF THE PREFERRED EMBODIMENT

Figure 1:
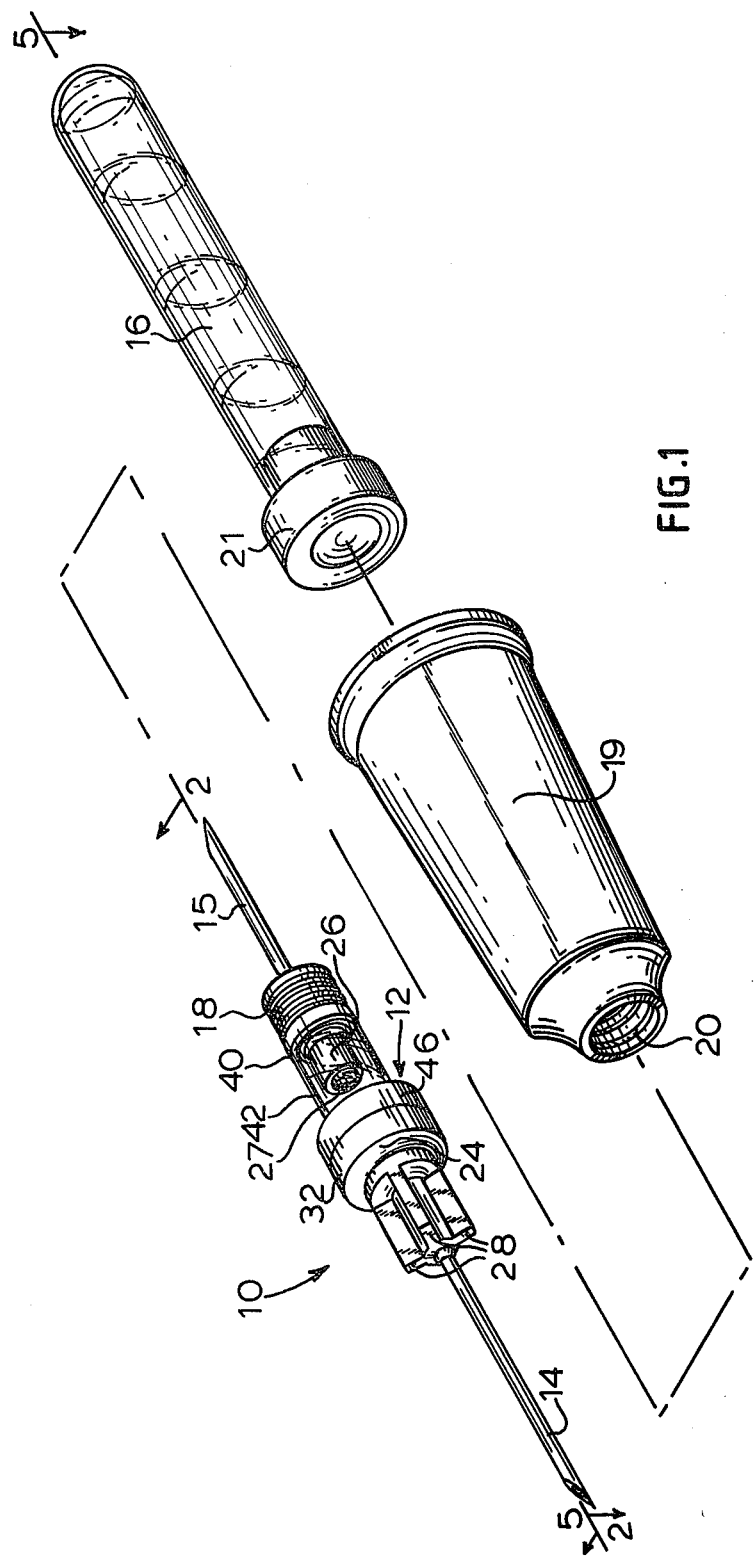
FIG. 1 is an exploded perspective view illustrating the preferred needle assembly, a holder for an evacuated container and an evacuated blood collection container for use in obtaining a blood sample from a patient.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Referring to the drawings, particularly FIG. 1, there is illustrated the embodiment of a preferred single sample needle assembly 10. The basic external components of needle assembly 10 include a housing 12, a first needle cannula 14 adapted for insertion into a patient and a second needle cannula 15 at the opposite end of housing 12, the second needle cannula adapted for penetration of an evacuated container 16 for collection of a blood sample. Housing 12 includes a threaded portion 18 adjacent second cannula 15 into which a container holder 19 is threaded by its internal mating threads 20 at the forward end of the holder. Evacuated container 16 slides into holder 19 so that second needle cannula 15 can penetrate the penetrable stopper 21 at the forward end of the evacuated container. These general aspects of blood sample collection in this type of structure are well known to those skilled in this art.

In FIGS. 2 and 3, the detailed construction of needle assembly 10 is illustrated. Housing 12 has a forward end 24 and a rearward end 25, these ends being preferably separable in order to place a vent plug 26 and a sealant plug 27 in their proper position within the housing. Forward end 24 is preferably cylindrically shaped and has a bore 29 preferably extending partially therethrough which is generally sized to slidably fit needle cannula 14 therein. In this embodiment being described, since bore 29 does not extend completely through forward end 24, a smaller diameter channel 30 communicates with bore 29 forming an access opening 31. At the junction between bore 29 and channel 30 a shoulder 33 is formed. Needle cannula 14 abuts against this shoulder for proper positioning. Once the needle cannula is in position, it may be suitably affixed such as by adhesive means or the like.

Forward end 24 of the housing also includes a number of longitudinal ribs 28 surrounding the outwardly extending cannula. A needle shield (not shown) generally covers the outwardly extending needle cannula and includes mating internal ribs within. The mating ribs between needle shield and needle assembly allow the user to facilitate the insertion or removal of the needle assembly into tube holder 19. Forward end 24 also includes an annular flange 32 which serves to provide a surface for joining the two portions of the housing together upon assembly. Once again, suitable fastening means, such as adhesives or the like, may be used to secure the two portions of the housing together.

Rearward end 25 is also preferably cylindrically shaped and includes a larger bore extending partially into one end of this portion. This bore serves as a chamber 40 within housing 12. A smaller bore 41 extends through the opposite end of rearward end 25 and is substantially similar to bore 29 in the forward end of the housing. Once again, bore 41 is sized to accept the diameter of second needle cannula 15, which is secured to bore 41 by appropriate means, including adhesives and the like. The outer portion of rearward end 25 surrounding bore 41 includes external threads 18 which are provided as previously mentioned as a connection mechanism to the tube holder. The outer portion 42 of rearward end 25 surrounding chamber 40 is preferably smooth and translucent or transparent so that a user of this assembly can view the interior of the housing. In many situations, it may be preferable to make the entire rearward end, and even possibly the forward end, out of translucent or transparent material for ease of manufacture and to minimize the different types of materials which may be used in this assembly. Translucent rigid plastic is the most desirable material for inclusion in this assembly. Various sealed windows, ports or other means for a user to view the contents of the chamber are within the purview of this invention. It is preferable that such window or port be sealed so that any blood which enters chamber 40 upon the needle entering the vein will not escape from this assembly.

Second needle cannula 15 which extends outwardly from rearward end 25 preferably extends through bore 41 so that it also has an integrally formed interior portion 44 extending inwardly into chamber 40, sufficiently far so that vent plug 26 is prevented from becoming disengaged therefrom. The distal end of this hollow needle cannula includes an opening 45 which is in fluid communication with the lumen of this hollow cannula. A side hole 48 is located through the side of interior portion 44 of this needle cannula and establishes fluid communication between chamber 40 and the lumen of this cannula. Rearward end 25 also includes an annular flange 46 which cooperates with flange 32 in joining the two ends of the housing together. Upon assembling forward end and rearward end together with vent plug 26 and sealant plug 27 placed in their proper positions, respective flanges 32 and 46 are secured together by appropriate fastening means, such as adhesives and the like. Vent plug 26 is placed inside chamber 40 so that it contacts the outer surface of interior portion 44 of the second cannula, in a liquid-tight engagement. Preferably, an annular gap 49 is left in chamber 40 between porous plug 26 and the wall 42 surrounding the chamber. This will allow the blood which initially enters the chamber upon venipuncture to occupy more volume thereby providing a better visual indicator to the user.

Vent plug 26 is preferably cylindrically shaped and is generally sized to fit in snug engagement around the surface of the interior cannula. This vent plug covers side hole 48 allowing air, but not blood, to pass into the side hole. The end of vent plug 26 facing toward the chamber at the distal end of the second cannula includes a pocket 50. Pocket 50 may be a counter-bore or counter-sink formed in the plug material, and is positioned so that it lies slightly above open end 45 at the distal end of the second cannula. This vent plug is made from a material intended to be gas-permeable, liquid-impermeable, and preferably air-permeable and blood-impermeable. These permeability properties would allow air to pass therethrough while preventing blood from flowing through this vent structure. Although other materials may be used, it is preferred that vent plug 26 be made of porous material, such as sintered polyethylene having a general pore rating of about ten (10) microns.

Sealant plug 27 is positioned over the distal end of interior portion 44 of the second cannula so that it covers and seals open end 45. Pocket 50 in the vent plug surrounds the sealant plug and facilitates its proper positioning at this distal end of the second cannula. Sealant plug 27 is preferably a mass of compliant material adapted to yield under a vacuum source applied to it. For example, when a negative pressure gradient is applied to plug 27 through the lumen of the second cannula, the sealant plug material should be able to be withdrawn through open end 45 and the second cannula toward the vacuum source. Once this occurs, the distal end of the second cannula will be open so that blood will be free to flow therethrough. Inasmuch as the preferred source of vacuum will be that from an evacuated blood collection container, such as illustrated in FIG. 1, the sealant plug material should be compliant enough to be withdrawn and removed from open end 45 under these vacuum conditions. Although many materials may be chosen, one such material for the sealant plug is a silicone grease, having a viscosity in the range of 400,000 to 500,000 cst. In addition, when choosing the sealant plug material, it should be kept in mind that this material will be drawn into the blood collection container just before the blood enters. Accordingly, the sealant plug material should be compatible with the blood, or other collected fluid, so that no harmful effects are imparted to the blood which is to be subsequently tested.

Turning now to FIG. 4, preferred needle assembly 10 is illustrated connected to a collection holder 19. At this stage of the blood collecting procedure, evacuated tube 16 is not yet attached while cannula 14 is initially inserted into patient P. At this stage, the sealant plug is in its position within the pocket of the vent plug at the distal end of the second cannula, covering the open end and effectively sealing same. Also at this stage, since no vacuum is being applied to needle cannula 15, the chamber and needles are substantially at atmospheric pressure conditions, so that there is air in the hollow portions of the needles and the chamber. Once vein entry has been made by needle cannula 14, blood will flow under normal tourniquet pressure through cannula 14 and will fill chamber 40. The air which was in this chamber is allowed to escape through the air-permeable material of vent plug 26. Air then enters side hole 48 and escapes through second needle cannula 15 which is open at its proximal end. As a result, blood may readily fill chamber 40 with no air blockage encountered as in prior art devices. Blood in the forward chamber is prevented from flowing into the second needle cannula due to both the liquid-tight seal formed by the blood-impermeable property of vent plug 26 and by the sealant plug 27 which covers the open distal end of the second cannula. In this regard, blood in the chamber can be viewed by a user through translucent portion 42 to have a visual indication that vein entry has been achieved by cannula 14. It should be pointed out that the force of blood flowing into the chamber under normal tourniquet pressure will not be sufficient to dislodge sealant plug 27 from its initially lying position over the open end of the second cannula.

Figure 5:
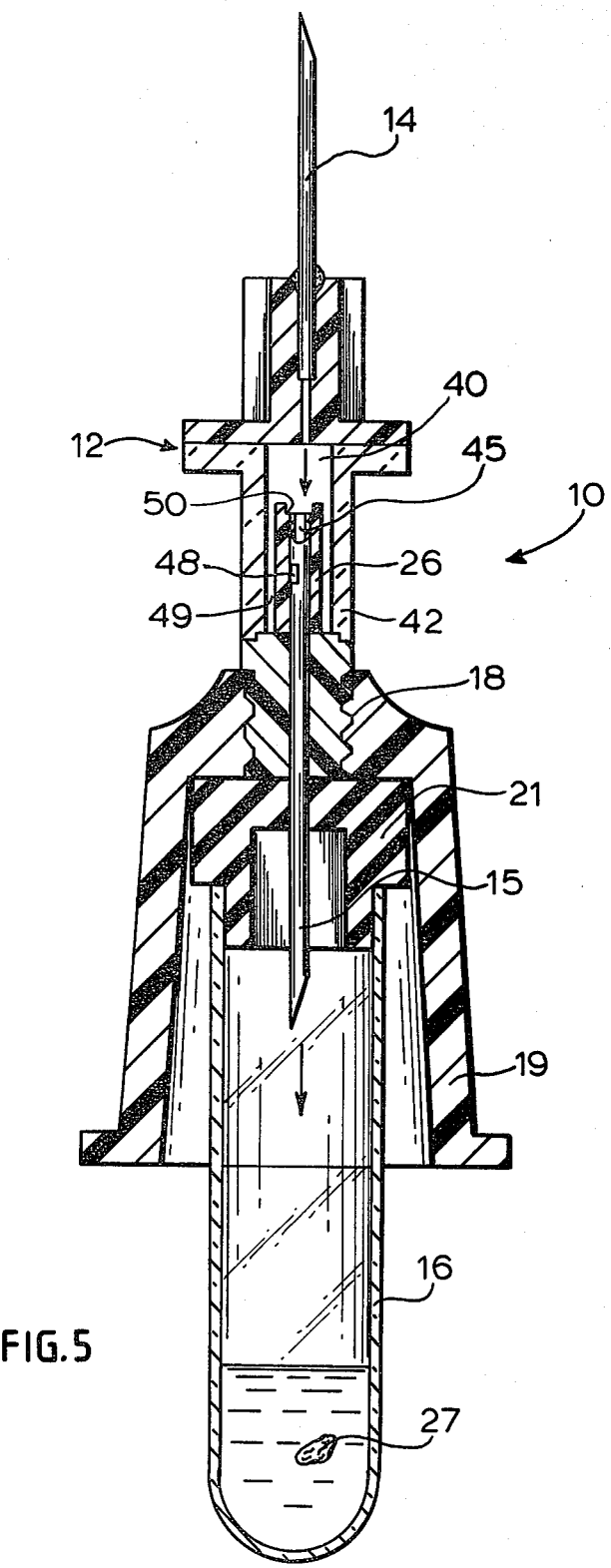
FIG. 5 is a cross-sectional view taken along line 5—5 of FIG. 1 with the components in an assembled condition as they would appear during use with the sealant plug removed so that blood can flow through the needle assembly into the collection container.

Once this visual observation of vein entry is confirmed by the user, evacuated tube 16 is then inserted into holder 19 so that penetrable stopper 21 is penetrated by hollow cannula 15. FIG. 5 illustrates this insertion of the evacuated blood collection tube. Once second cannula 15 is into the vacuum area inside container 16, a negative pressure gradient is transmitted into hollow cannula 15. Under the influence of this negative pressure gradient, compliant sealant plug 27 is drawn into the lumen of cannula 15 toward the source of the negative pressure and will be deposited into the blood collection container. The effect of this sealant plug removal causes opening 45 to become uncovered, with a free path for blood inside chamber 40 to flow into the second needle cannula. Blood will now flow through the needle assembly and into the blood collection container until a sufficient quantity has been collected, whereby the blood sample procedure is terminated by removal of needle cannula 14 from the vein of the patient.

Thus, the needle assembly of the present invention includes vent and plug means which are easily mounted in the assembly and allow air to escape from the assembly during the initial venipuncture step as vein entry is being determined. With this air escapement feature, a blood trace upon vein entry will immediately flow into the chamber of the present needle assembly with a visual indicator feature being provided to the user to take cognizance of vein entry. With this assurance of vein entry, the blood collection container can be satisfactorily filled for collection of the sample from the patient.

What is claimed is:

1. A needle assembly for collecting a single blood sample from a patient for introduction into an evacuated container, comprising
   (a) a translucent housing having a forward end and a rearward end;
   (b) a chamber in said housing;
   (c) a first access opening in said forward end;
   (d) a first cannula in fluid communication with said chamber and extending outwardly from said first access opening and adapted for insertion into a patient;
   (e) a second cannula in fluid communication with said chamber and extending outwardly from said second access opening; the improvement characterized by
   (f) said second cannula having a portion on the end thereof opposite to that extending outwardly from said second access opening, which extends internally into said chamber;
   (g) said internally extending portion having a first and a second hole therethrough, with said second hole providing fluid communication between said chamber and the lumen of said second cannula;
   (h) a vent plug of air-permeable, blood-impermeable material in liquid-tight contact with the outer surface of such internally extending portion and overlying said first hole;
   (i) means for temporarily restricting blood flow covering said second hole; and
   (j) said temporary restricting means comprising a compliant material forming a sealant plug permanently displaceable from covering said second hole by a negative pressure gradient applied to said second cannula, and being sufficiently pliable to deform and pass through the lumen thereof;
   (k) whereby blood flowing into said chamber from said first cannula under normal tourniquet pressure is prevented by said plugs from flowing into said second cannula, but can be viewed through said translucent housing to indicate vein entry by said first cannula while air in said chamber passes through said vent plug and first hole and through said second cannula, and said sealant plug being drawn through said second hole and the lumen of said second cannula when said pressure gradient is applied for allowing blood to flow through said second cannula for collection.

2. The assembly of claim 1 wherein said first hole is through the side of said second cannula and said second hole is at the distal end of said second cannula.

3. The assembly of claim 1 wherein said vent plug is a hollow cylinder and forms a pocket around the distal end of said second cannula to facilitate the placement of the sealant plug on said second hole.

4. The assembly of claim 1 wherein said vent plug material is sintered polyethylene having a general pore rating of about ten (10) microns.

5. The assembly of claim 1 wherein said material of said sealant plug is silicone grease having a viscosity rating of about 400,000 to 500,000 cst.

6. The assembly of claim 1 which further includes a holder for an evacuated container connected to said housing.

* * * * *